United States Patent
Despa et al.

(10) Patent No.: US 12,042,641 B2
(45) Date of Patent: *Jul. 23, 2024

(54) METHOD AND DEVICE FOR CAPTURING A DOSE DIALING EVENT

(71) Applicant: Becton, Dickinson and Company, Franklin Lakes, NJ (US)

(72) Inventors: Mircea Stefan Despa, Cary, NC (US); Harry Bullivant, Cambridge (GB); Andrew Richards, Durham, NC (US); Michael Allan, Islington (GB); Mark Hsieh, Cambridge (GB); Sundeep Kankanala, Chapel Hill, NC (US); Dylan Wilson, Chapel Hill, NC (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/170,394

(22) Filed: Feb. 16, 2023

(65) Prior Publication Data

US 2023/0277775 A1  Sep. 7, 2023

Related U.S. Application Data

(63) Continuation of application No. 16/384,774, filed on Apr. 15, 2019, now Pat. No. 11,583,635, which is a (Continued)

(51) Int. Cl.
*A61M 5/315* (2006.01)
*G16H 20/17* (2018.01)

(52) U.S. Cl.
CPC ...... *A61M 5/31548* (2013.01); *A61M 5/3155* (2013.01); *A61M 5/31568* (2013.01); (Continued)

(58) Field of Classification Search
CPC .......... A61M 5/31548; A61M 5/3155; A61M 5/31568; A61M 2205/3375
See application file for complete search history.

(56) References Cited

U.S. PATENT DOCUMENTS

2009/0069742 A1  3/2009  Larsen
2011/0060455 A1  3/2011  Bogash et al.
(Continued)

FOREIGN PATENT DOCUMENTS

EP    2692378 A1    2/2014
WO   WO 2010/037828   4/2010
(Continued)

OTHER PUBLICATIONS

International Search Report and Written Opinion mailed Apr. 1, 2016 from International Application No. PCT/US2016/014304 filed Jan. 21, 2016, 13 pgs.

*Primary Examiner* — Dung T Ulsh
(74) *Attorney, Agent, or Firm* — Knobbe, Martens, Olson & Bear LLP

(57) ABSTRACT

Disclosed are systems and methods of detecting an impulse of energy given off by an injection device and determining a dosage of medicine based on the impulse. In one example, a module detects the vibrations given off by dialing a click-wheel on an autoinjector and determining the selected dosage of medicine based on the dialed dosage.

21 Claims, 8 Drawing Sheets

Related U.S. Application Data continuation of application No. 15/003,393, filed on Jan. 21, 2016, now Pat. No. 10,258,745.

(60) Provisional application No. 62/107,023, filed on Jan. 23, 2015.

(52) U.S. Cl.
CPC ..... *G16H 20/17* (2018.01); *A61M 2205/3331* (2013.01); *A61M 2205/3375* (2013.01); *A61M 2205/50* (2013.01)

(56) References Cited

U.S. PATENT DOCUMENTS

| | | |
|---|---|---|
| 2011/0295215 A1 | 12/2011 | Nielsen |
| 2014/0142544 A1 | 5/2014 | Atterbury et al. |
| 2014/0207080 A1 | 7/2014 | Allerdings |
| 2018/0280624 A1* | 10/2018 | Bitton ................. A61M 5/3155 |

FOREIGN PATENT DOCUMENTS

| | | |
|---|---|---|
| WO | WO 2012/152628 | 11/2012 |
| WO | WO 2014/064691 | 5/2014 |
| WO | WO 2014/111337 | 7/2014 |

* cited by examiner

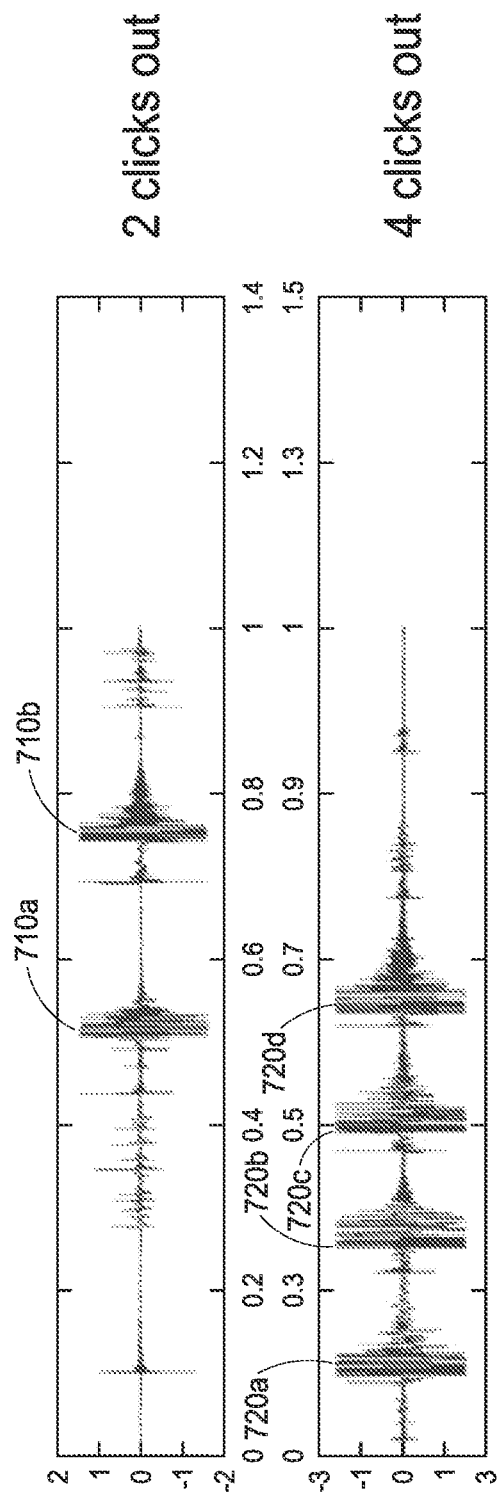
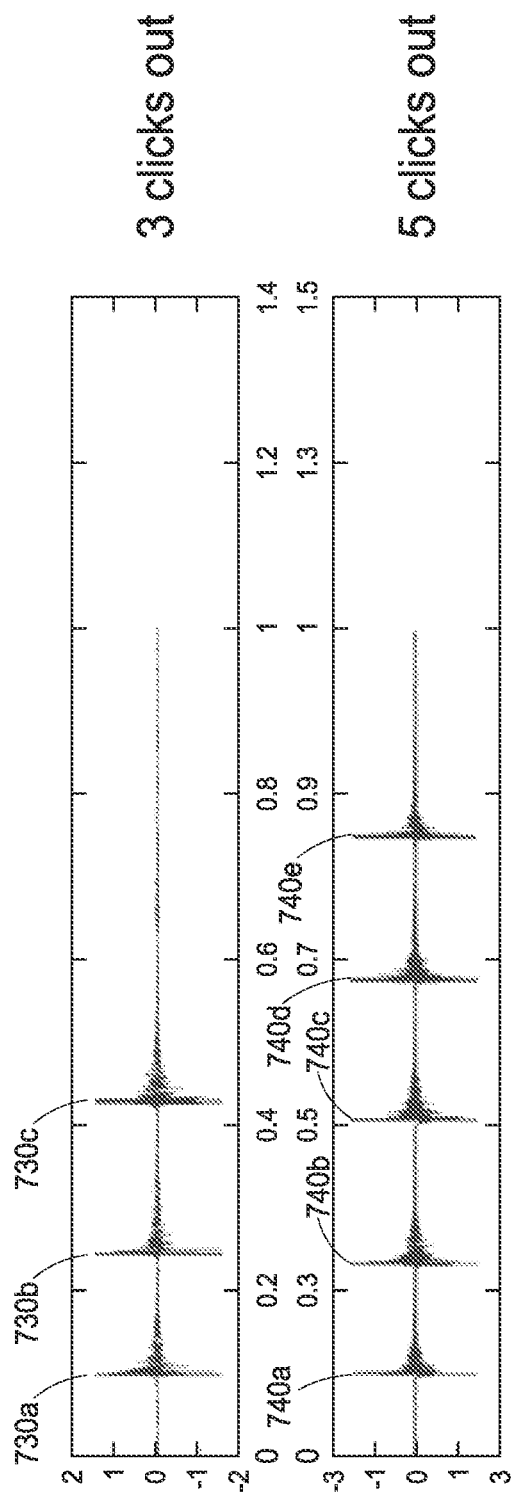

METHOD AND DEVICE FOR CAPTURING A DOSE DIALING EVENT

INCORPORATION BY REFERENCE TO ANY PRIORITY APPLICATIONS

This Application is a continuation of U.S. application Ser. No. 16/384,774, entitled METHOD AND DEVICE FOR CAPTURING A DOSE DIALING EVENT and filed on Apr. 15, 2019, which is a continuation of U.S. application Ser. No. 15/003,393, entitled METHOD AND DEVICE FOR CAPTURING A DOSE DIALING EVENT and filed on Jan. 21, 2016, which claims priority to U.S. Provisional Application No. 62/107,023, entitled "METHOD AND DEVICE FOR CAPTURING A DOSE DIALING EVENT" and filed on Jan. 23, 2015, each of which are incorporated by reference in their entirety.

BACKGROUND

Field

The invention relates to injection devices, and more particularly, relates to methods and devices for detecting a dose of medicament selected on an injection device. More particularly, the invention relates to methods and devices that measure motion or vibration of an injection device to determine what dose of medicament has been selected for injection by a user.

Description of the Related Art

Injection devices are medical devices that allow patients to self-administer their medications outside a hospital or physician's office. These devices are often used for the management of chronic diseases. A typical injection device has a prefilled syringe in a mechanical device that deploys a needle and delivers a medicament with a single push of a release button. The user of a typical injection device is able to select the amount of medicament to be delivered. Injection devices may also be disposable, and can include safety mechanisms to shield the needle both before and after injection.

In order to manage the chronic disease effectively, self-administering patients maintain a log or history of numerous aspects of their daily lives. As part of the log, patients are expected to memorize and record the amount of medicament and the time of each injection, along with eating habits and exercise routines. A missing or erroneous record in the log may create result in incorrect injection information being stored. This can lead the patient to mis-administer future doses of their medicine along with leading medical personnel to make improper decisions with respect to future medication regimens.

To overcome some of these disadvantages, prior injection devices have included optical, capacitive, magnetic or similar methods to detect how much medicine has been injected by the patient. However, these prior approaches result in devices that are large in size, rendering the device bulky and ergonomically unattractive. Some prior injection devices were also designed in a way that affected how the user interacted with the injection device, for example, by introducing a new dose dialing button not originally designed for the injection device. Other prior injection devices detect the dose based on determining the position of a stopper inside the pre-filled cartridge before and after injecting medicament. However, these methods did not provide an ability to determine the direction of or the number of multiple individual dosing events that occur between measurements.

SUMMARY

One aspect of the invention is a method for detecting an impulse of energy given off by an injection device, determining a dosage of medicine based on the impulse, and communicating that information to a patient. In this embodiment, a module is configured to detect an impulse of energy given off by selecting a dose of medicine and determine the selected dose based on the direction and magnitude of the impulse.

One embodiment is a method for detecting at least one dialing event of an injection device. The method may include: detecting an impulse transmitted through the injection device, where the impulse is related to at least one external event; determining event parameters based on the impulse; and determining the external event is a dialing event based on event parameters.

The foregoing and/or other aspects of the present invention are achieved by providing a module containing one or more sensors related to vibrations and directional motion transmitted to the injection device that can be attached to the body of an injection device.

In another embodiment of the present invention, data related to the at least one dialing event of the injection device can be transmitted to an external device.

Another embodiment of the present invention is a module for detecting dose dialing parameters. The module may include: a carrier configured to mate with an injection device; one or more sensors mounted on the carrier; and a processor configured to read parameters and detect a dialing event based on the parameters.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 1A is a perspective view of one embodiment of an injector with an attached external module. FIG. 1B is a side perspective view of an injector with an adjacent external module. FIG. 1C is a lower perspective view of an injector with an adjacent external module.

FIG. 7A-D depict graphs illustrating dose dialing event signatures in accordance with an illustrative embodiment of the present invention.

DETAILED DESCRIPTION

Figure 1:
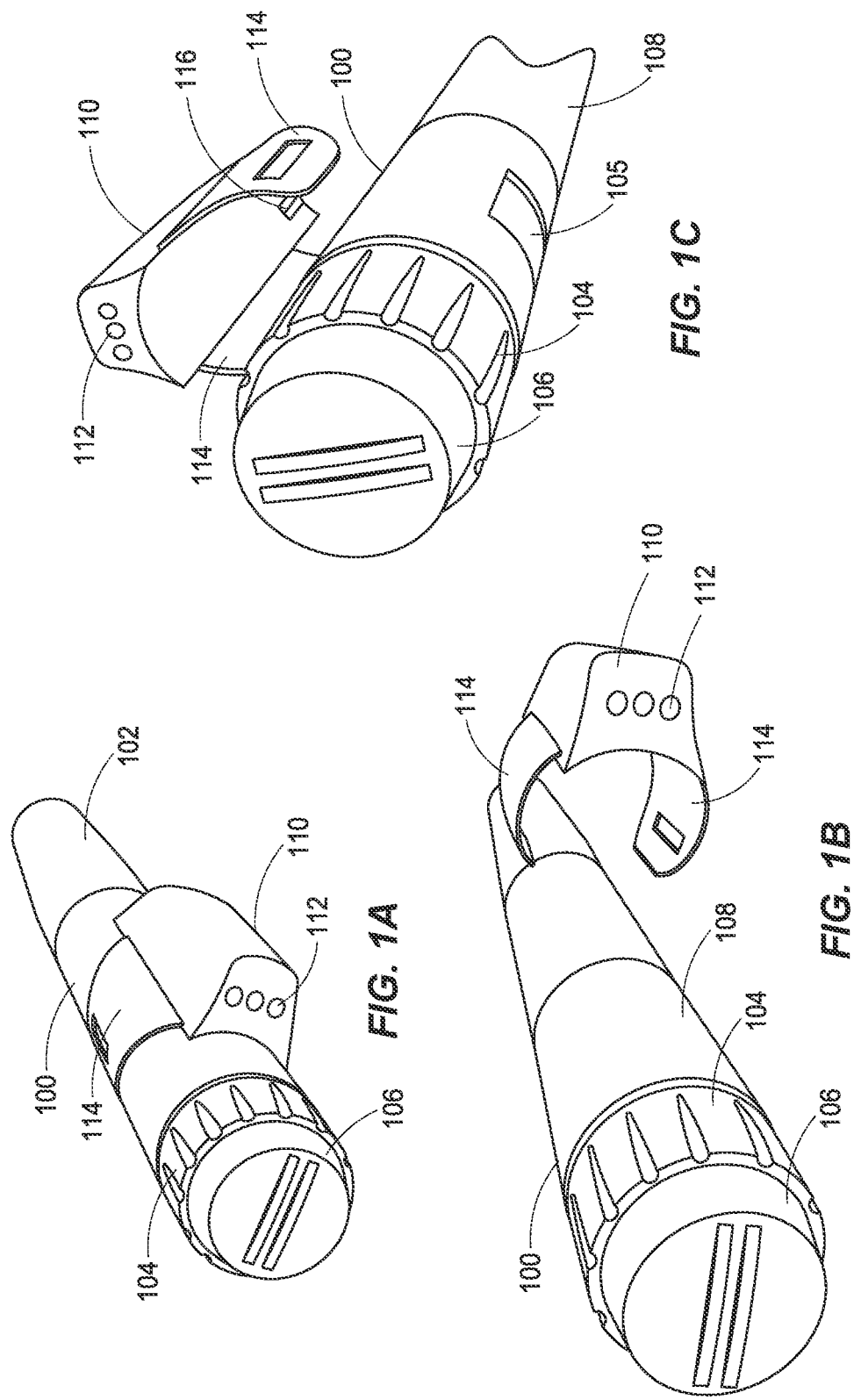
FIGS. 1A-C depict an injection device with a module in accordance with an illustrative embodiment of the present invention.

As will be appreciated by one skilled in the art, there are numerous ways of carrying out the examples, improvements, and arrangements of a medicament delivery device or injection device in accordance with embodiments of the present invention. Although reference will be made to the illustrative embodiments depicted in the drawings and the following descriptions, the embodiments disclosed herein are not meant to be exhaustive of the various alternative designs and embodiments that are disclosed. Those skilled in the art will readily appreciate that various modifications may be made, and various combinations can be made, without departing from the invention.

Embodiments of the device and methods for detecting dose dialing event parameters on an injection device are discussed herein and are described below in further detail in connection with FIGS. 1-8. One embodiment includes a module designed to attach to the external body of an injection device, e.g., an autoinjector, disposable injection device, or durable injection device having interchangeable pre-filled cartridges. For example, the device may be adapted to attach to the PHYSIOJECT™ autoinjector, VYSTRA™ Disposable Pen, or Reusable Pen from Becton Dickinson®. In this embodiment, the module is configured to attach to the exterior of the injection device. This allows for the module to be designed as a compact, lightweight, low power and low cost module for detecting a dialed dose. As a user rotates a dial on the injector device, the module detects parameters associated with the rotation, and determines the dose selected by the user. As will be discussed in more detail below, the module may detect motion or vibrations associated with the dialing process, and then discriminate from that data the precise dosage selected by the user on the injection device.

Another embodiment includes a module integrated into a safety cap of an injection device. In this embodiment, the module can be initially designed into the cap and placed on the injection device replacing the original cap.

In an illustrative embodiment, the module can include one or more sensors capable of monitoring and detecting external events associated with the use of an injection device. This can include sensors for orientation, motion, directional movement, sound, and vibrations experienced by the injection device due to an external event. The module may detect the direction of motion and vibrations of the external event before use of the injection device, during use of the injection device, and after use of the injection device. The module can also include a microprocessor configured to process data from the sensors to determine whether an external event is a dose dialing event or an extraneous event that could be mistaken for a dose dialing event, e.g., an accidental knock of the injection device. Once a dose dialing event is detected, the microprocessor may determine a total selected dosage based on the direction and/or number of multiple dose dialing events that occur while a user selects an appropriate amount of medicament to be administered.

The processor may be programmed or configured to determine a set of event parameters based on data from the sensors. For example, injection devices such as insulin pens, used to manage diabetes, are designed to produce feedback related to a sudden release of mechanical energy every time a dose is selected. The release of mechanical energy manifests to the user through audible clicks and tactile feedback. Within the injection device, the release of mechanical energy results in overall motion and vibrations transmitted through the injection device body or the internal air spaces. The sensors in the module are configured to detect the release of mechanical energy, and the microprocessor may be configured to analyze data from the sensors to determine the magnitude of the dialing event. Similarly, the sensors may detect a direction of net inertial force related to the impulse of energy, and the processor may be programmed to analyze the data from the sensors to distinguish between a dose increasing event (e.g., "dialed up") and a dose decreasing event ("dialed down").

The processor may also be programed or configured to determine if the event parameters exceed a predetermined threshold. For example, the magnitude and direction of the force due to an accidental knock may be represented by a specified threshold value. In one embodiment, the threshold value can be determined experimentally by performing a representative number of controlled studies to isolate dose dialing events from any extraneous disturbances or events. The controlled studies can include measuring and/or monitoring controlled dose dialing events ("clicks"). In one embodiment, the threshold value can be determined as the lowest value of any of the controlled dose dialing events. In another embodiment, the threshold value may be determined as an average value of the controlled dose dialing events. In one embodiment, the threshold value is specified as a formula that represents the characteristics that event parameters must exceed for the processor to recognize the external event as a dose dialing event. For example, the processor may be programmed or configured to analyze the data from sensors due to the external event, determine the event parameters of the external event, and compare the event parameters with the threshold value. If the comparison shows the event parameters do not exceed the threshold value and, therefore, are not associated with a dose dialing event, then the processor rejects the event, e.g., when an accidental knock is detected by the sensors. Accordingly, if the processor determines that the event parameters exceed the threshold value, then the processor may be configured to classify the external event as a dose dialing event.

The processor may be further programmed or configured to count, or track, the number and direction of dose dialing events to determine a total selected dose for a given injection of medicament ("injection event"). The processor may determine whether an external event is a dialing dose event and the direction of the dose dialing event (e.g., dialing up or dialing down). For example, in selecting a dose of medicament of two units, a user may operate a dose dialing mechanism by dialing up three doses, thereby increasing the selected dose by three units. The user may then realize the error and operate the mechanism by dialing down a single unit to reach the desired dosage of two units. The processor may be programmed or configured to determine the occurrence of each dose dialing event based on event parameters as explained herein. Further, based on the event parameters, the processor may be programmed or configured to differentiate between a dialed up dose dialing event and a dialed down dose dialing event. The processor may accept the event parameters and apply an algorithm to determine a total selected dose.

In an illustrative embodiment according to the present invention, the module may further include a communication module to allow for connectivity between an injection device and external devices. The communication module can transmit information from the module to interested parties including the patient, payers, pharmacies and clinicians. For example, prior to use, the module may be connected to an application running on a portable electronic device, such as a smart phone or tablet. This connection may be made using well-known wireless communication protocols, such as Bluetooth®, WIFI, or other means. Once the application detects a connection to the module, data from the on-board sensors may be transmitted to the application for display to the user. For example, the total selected dose for an injection event and the time of that the total selected dose was selected may be displayed. In another embodiment, a chart or graph showing the measured event parameters may be displayed to the user. In another embodiment, a history or log of injection event times and total selected dose may be displayed for a given period of time, e.g., the previous day, week, month, etc.

As mentioned above, the module may be configured and shaped to retrofit a pre-existing injection device. The module may be placed along the body an injector so that the placement of the module does not prevent activation or movement of any of the pre-existing functions of the injection device. Further, the module may include an electronic switch or lever that is activated upon the occurrence of an activation event. In this regard, an activation event may be the attachment of the module to the body of the injection device or occurrence of an external event. Thus, in one embodiment the module can detect when the injection device has been activated by the user to administer medicament. This allows additional functionality to be designed into the module. For example, upon detection of the activation event, the smart module can transmit a signal to any connected external device. The external device may be a computer, or portable electronic device that records the time and date of the activating in order to help the user track when the injections have taken place.

In one embodiment, the module is placed within an insulin injection device that is configured to administer insulin to a diabetic patient. Upon administration the module may detect the injection event, and transmit a signal to an electronic device running a software program that tracks dose dialing event parameters and injection event information for the patient. Because diabetic patients typically administer insulin several times a day, this provides a simple and efficient mechanism to allow them to track a day and time of their insulin injections. In some embodiments, the module may detect the amount of insulin given from the injection device.

In an illustrative embodiment, the injection device may be disposable. In some embodiments of the present invention, the module may be disposable as well. In other embodiments, the module may be removed and placed on a different disposable injection device to continue monitoring medicament administered while switching between different injection devices. In yet another embodiment, the module may be designed into a safety cap or other element protecting the needle for administering medicament. In this embodiment, the module may be included in the cap from the original design, replacing the original cap, and enabling development of a smart cap that further avoids interfering with the any of the pre-existing functions of the injection device.

In the following description, specific details are given to provide a thorough understanding of the examples. However, it will be understood by one of ordinary skill in the art that the examples may be practiced without these specific details. For example, electrical components/devices may be shown in block diagrams in order not to obscure the examples in unnecessary detail. In other instances, such components, other structures and techniques may be shown in detail to further explain the examples.

It is also noted that the examples may be described as a process, which is depicted as a flowchart, a flow diagram, a finite state diagram, a structure diagram, or a block diagram. Although a flowchart may describe the operations as a sequential process, many of the operations can be performed in parallel, or concurrently, and the process can be repeated. In addition, the order of the operations may be re-arranged. A process is terminated when its operations are completed. A process may correspond to a method, a function, a procedure, a subroutine, a subprogram, etc. When a process corresponds to a software function, its termination corresponds to a return of the function to the calling function or the main function.

Those of skill in the art will understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Although various persons, including, but not limited to, a patient or a healthcare professional, can operate or use illustrative embodiments of the present invention, for brevity an operator or user will be referred to as a "user" hereinafter.

Although various fluids can be employed in illustrative embodiments of the present invention, fluid in an injection device will be referred to as "medicament" hereinafter.

Although various inputs, including, but not limited to, mechanical buttons, tactile inputs, voice-controlled input, or any other inputs known in the art, can be implemented using illustrative embodiments of the present invention, for brevity an input will interchangeably be referred to as a "button" or a "trigger" hereinafter.

FIGS. 1A-1C depict an illustrative embodiment of an injection device 100. The injection device 100 includes an elongated cylindrical body 108 having an injecting button 106 positioned on one end of the injection device 100. Injecting button 106 activates the injection device to release a syringe (not shown) into a user. Thus, when the injecting button 106 is engaged, the syringe inside the injection device 100 is deployed so that medicament is injected into the user. At the distal end of body 108 is a safety cap 102 configured to prevent the user from inadvertent contact with the syringe.

Injection device 100 is also fitted with a dose dialing mechanism 104. In the embodiment shown in FIG. 1A, dose dialing mechanism 104 is depicted near the injecting button 106. However, it should be realized that the position of dose dialing mechanism 104 may be positioned anywhere along the injection device body 108. Dose dialing mechanism 104 is configured to allow the user to easily and readily dial an injection volume or dose. For example, the user may operate the dose dialing mechanism 104 to dial, either increase or decrease the amount of medicament.

The injection device 100 also includes a viewing window 105 (FIG. 1C) that allows the user to see the amount of medicament selected by the dose dialing mechanism 104. In one embodiment, viewing window 105 may show a volume of medicament. In another embodiment, viewing window 105 may show an increment of medicament equal to a single dose, such that each dose is a single unit equal to an amount of medicament as predicated by the user's particular medical regimen.

The operation of dose dialing mechanism 104 is configured to produce tactile and audible feedback occurring at each dose increment, typically one unit. In one embodiment, the tactile feedback may be felt by the user as a result of two elements temporarily interfering with each other that are suddenly released, causing mechanical energy feedback felt by the user. In another embodiment, the incremental adjustment of medicament dose results in an audible and tactile "click" corresponding to each dialed dose increment. The tactile and audible feedback can be heard and felt by the user when operating dose dialing mechanism to increase or to decrease the dosage.

In yet another embodiment, the dose dialing mechanism 104 can by designed to include at least two members, a toothed crown and a cam (not shown), which move relative to each other. In this embodiment, the two members interfere with each other every time a dose increment is dialed by the user. The interference is periodically interrupted at each dose increment, resulting in a temporary and abrupt release of mechanical energy. This release or impulse of mechanical energy is then transmitted through the pen body and the surrounding air to generate the audible and tactile feedback.

FIG. 1 also depicts dose detection module 110 attached to the exterior of injection device body 108. The dose detection module 110 is configured to rigidly couple to body 108 and includes at least one sensor to detect the release of mechanical energy, including the direction and magnitude parameters of the impulse. Once detected, these parameters are filtered and interpreted by an algorithm thereby determining the dosage selection direction, e.g., dialed up or down, as well as the incremental change in dosage.

Module 110 includes at least one coupling bracket 114 to rigidly attach dosage detection module 110 to injection device body 108. In one embodiment, module 110 may be cylindrical in shape and configured to reversibly mount to the exterior shell or cap of the injection device 100. In one embodiment, the module 110 may include tabs, snaps, brackets, or other means for mounting to the injection device 100.

In the embodiment shown in FIG. 1, coupling bracket 114 comprises two tangs shown to mate (and detach) module 110 to injection device body 108 by clamping (or other method known in the art) to provide a secure fit. The module 110 can be made to fit along the injection device body 108 in a manner and location where the pre-existing functions of the injection device 100 are not affected. In one embodiment, the module may be affixed to body 108 away from dose dialing member 104 and viewing window 105.

In an illustrative embodiment according to the present invention, the dose detecting module 110 allows for a user to view one or more status indicators 112 located on the module 110. The one or more status indicators 112 may be part of the module 110 and can indicate a condition or state of the device. The status indicators 112 may include one or more lights, such as light-emitting diodes ("LEDs") or any other visual, auditory, or tactile stimuli. The condition or state of use may include, but is not limited to, out-of-range conditions (e.g., a loss of connectivity) or temperature alerts.

In another illustrative embodiment according to the present invention, the module 110 may include a microswitch 116. Microswitch 116 may be operated to activate module 110. In one embodiment, microswitch 116 may be operated upon attaching module 110 to injection device 100. In this regard, the module 110 is activated as soon as it is attached to the injection device 100 and continuously monitors external events until powered off or removed from the injection device 100. In another embodiment, the user may actively operate microswitch 116 by pressing the button to turn the module 110 on or off as desired.

It should be realized that the injection device 100 can function to inject medicament into the user without the presence of the module 110. The module 110 is designed to add electronic monitoring and reporting capabilities to the pre-existing injection device. Thus, the module 110 can be attached to the injection device 100 after manufacture, without changing the pre-existing functions of injection device 100. In an illustrative embodiment according to the present invention, the injection device 100 can be the PHYSIOJECT™ autoinjector, VYSTRA™ Disposable Pen, or Reusable Pen from Becton Dickinson. Although it should be realized that other injector devices are also contemplated within the scope of the invention.

Figure 2:
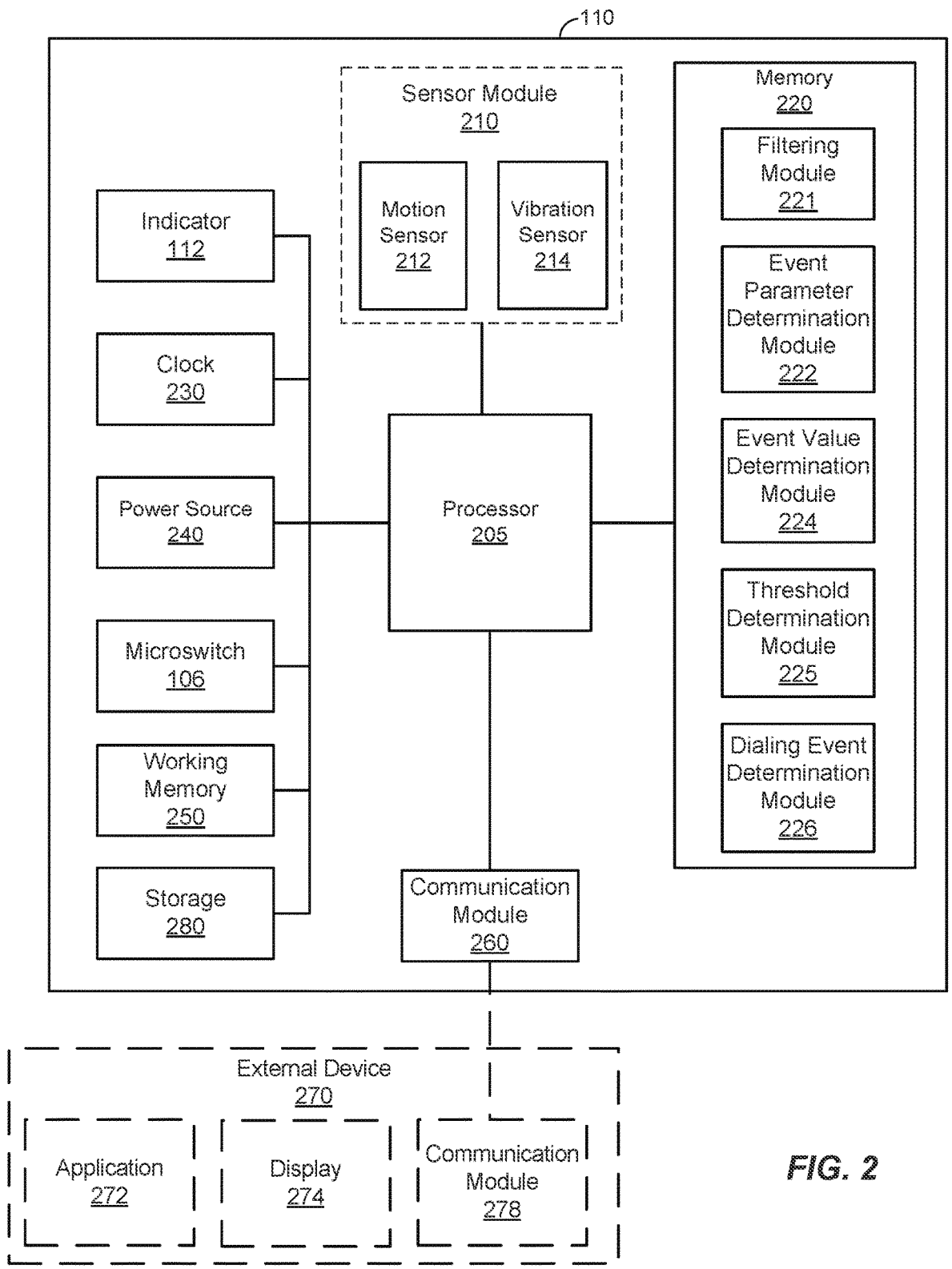
FIG. 2 depicts a schematic view of a module in accordance with an illustrative embodiment of the present invention.

FIG. 2 depicts a schematic view of the elements within the dose detection module 110 in accordance with one embodiment. The module 110 is configured to monitor and detect external events and characteristics associated with the dialing of a dose of an injection device. The module 110 can also communicate the various external events and characteristics of the injection device to a user through visual, auditory, or tactile stimuli or can transmit to an external device 270.

In an illustrative embodiment according to the present invention, the module 110 comprises a processor 205 that is in electrical communication with a sensor module 210. The sensor module 210 includes a motion sensor 212 and vibration sensor 214. The processor 205 is also connected to an indicator 112, a clock 230, a power source 240, a microswitch 106, storage 280, and working memory 250. In addition, the processor 205 is connected to a memory 220 having modules that store data values defining instructions to configure processor 205 to perform the functions of module 110. The memory 220 includes a filtering module 221, an event determination module 222, an event value determination module 224, a threshold determination module 225, and a dialing event determination module 226. In one embodiment, processor 205 is also connected to a communication module 260 that is in wired or wireless communication with an external device 270. External device 270 includes a communication module 278, an application 272, and a display 274. It should be realized that these components can be mounted within the module 110 while allowing the module 110 to attach to the injection device.

In an illustrative embodiment according to the present invention, data from sensor module 210, e.g., sensor data, may be recorded, transmitted, or indicated through a series of steps. In one illustrative embodiment according to the present invention, sensor module 210 is activated when microswitch 106 is activated. In response, sensor module 210 detects the occurrence of an external event and generates sensor data which is transmitted from sensor module 210 to processor 205. In one embodiment, processor 205 then performs on-board processing using instructions from memory 220 to determine whether the external event is a dose dialing event. In one embodiment, the processor 205 determines whether one or more event parameters exceed a predefined threshold. In an alternative embodiment, sensor data from sensor module 210 can be recorded in memory 250 and transmitted to external device 270. In another embodiment, processor 205 is configured to determine the number of dose dialing events and direction of each dialing event to determine a selected dose for an injection event.

In an illustrative embodiment according to the present invention, sensor module 210 includes sensors configured to detect an external event, e.g., an event external to module 110. For example, sensor module 210 may include motion sensor 212 and vibration sensor 214 configured to detect, but not limited to, movement, orientation, vibrations, and sound resulting from a user operating the dose dialing mechanism 104 of injection device 100. In another embodiment, sensor module 210 may include sensors for detecting temperature, proximity, and amount of medicament present in or injected by an injection device. In one embodiment, motion sensor 212 and vibration sensor 214 comprise a single axis accelerometer configured relative to the injection device body such that the accelerometer can sense movements imparted on the injection device body resulting from an external event. In this regard, the single axis accelerometer may be oriented perpendicular to the long axis of the injection device. In another embodiment, motion sensor 212 and vibration sensor 214 comprise multiple accelerometers, e.g., single axis and/or 3D accelerometers, thereby enabling detection of direction movement and vibrations in a multiplicity of directions and increasing detection sensitivity.

In another embodiment, sensor module 210 can include additional sensors for detecting state of device data. In one embodiment, sensor module 210 may comprise a microphone to detect audible variations occurring around module 110. For example, a microphone can be used to detect sounds specific to other functions of the injection device, such as, but not limited to, the injection of medicament, the click sound associated with the dose dialing mechanism, or other sounds unique to operating an injection device. In another embodiment, sensor module 210 may include a temperature sensor that detects temperature experienced by the injection device during use, storage, or after use of the injection device. In this regard, sensor data from a temperature sensor may be transmitted to indicator 112 to notify the user of state-of-device information based on the temperature data. In yet another embodiment, sensor module 210 can include a proximity sensor. In an embodiment utilizing a proximity sensor, the sensor module 210 may detect out-of-range conditions of module 110. For example, out-of-range conditions may include, but are not limited to, proximity of the module 110 to the injection device, proximity of the module 110 to an external device 270, or a loss of data connectivity in communication module 260. Sensor module 210 may then transmit out-of-range data to indicator 112 which may notify the user of the existing condition through any form of stimuli, for example, visual light, audible, or tactile notifications.

In another embodiment, sensor module 210 may include additional sensors configured to provide additional sensing to assist evaluating an external event. For example, a microphone can be used to detect sounds that are unique to the injection device functions, e.g., removing of the safety cap or the use injection of medicament. Such sounds may indicate that the detected external event relates to an extraneous event (e.g., an injection event) opposed to a dose dialing event. In another embodiment, an additional accelerometer can be used to detect the removal of the safety cap prior to administering a dose. In yet another embodiment, additional accelerometers can also be used to detect injection device orientation, e.g., motion and orientation, typically associated with an injection event. It should be realized that although illustrative examples are provided herein, the sensor module 210 can be configured with any sensor known in the art configured to indicate and support the determination of whether an external event is the result of a dose dialing event, an extraneous event, or general injection device usage.

In an illustrative embodiment according to the present invention, processor 205 is also connected to indicator 112. In response to sensor module 210, indicators 112 can indicate a state of the device to the user. For example, when indicator 112 comprises one or more LEDs, one or more LEDs may be activated and emit light in response to sensor data. In another embodiment, the indicator 112 can notify a user of a condition or state of the device. Examples of conditions or states of the device include, but are not limited to, ready-to-use, not-ready, fault, refrigerated, etc. The one or more LEDs may indicate different conditions to a user through color, duration, or repetition of light emission.

In an illustrative embodiment according to the present invention, processor 205 is connected to a clock 230 or the like included in module 110. The clock 230 may continuously update the internal time in memory 220 and working memory 250 of the module 110. The processor 205 can continuously check the internal clock 230 and compare with the data obtained from sensor module 210 or memory 220 while processing the algorithm further described herein.

In an illustrative embodiment according to the present invention, processor 205 is connected to power source 240. The power source 240 provides power to remaining portions of the module 110. In one embodiment, power source 240 may be a battery included in module 110. In this embodiment, the module 110 may be configured to have enough power and battery life so that it can monitor for weeks, months, or years during the operation of injection device 100. In another embodiment, power source 240 may be a source located externally to module 110, e.g., on injection device 100 or other external location.

In an illustrative embodiment according to the present invention, processor 205 is connected to a microswitch 106. The microswitch 106 can be activated at the time that the module 110 is attached to an injection device or at the time that an injection event occurs. Upon activating the module 110, power source 240 supplies power to module 110 activating the various components of module 110, including processor 205.

In an illustrative embodiment according to the present invention, processor 205 can be configured to store or transmit data to working memory 250 and/or storage 280. The working memory 250 may be utilized by the processor 205 to store data dynamically created during operation of the module 110. For example, instructions from a module stored in memory 220 may be stored in working memory 250 when executed by the processor 205. The working memory 250 may also store dynamic run time data, such as stack or heap data utilized by programs executing on processor 205. The storage 280 may be utilized to store data created by module 110. For example, event parameters or dose dialing events may be stored on storage 280. In another embodiment, sensor data from sensor module 210 can be stored in working memory 250 and/or storage 280 or transmitted to an external device 270 via communication module 260.

In an illustrative embodiment according to the present invention, memory 220 may be considered a computer readable media and stores several modules. The modules store data values defining instructions for processor 205. These instructions configure the processor 205 to perform functions of module 110. For example, in some aspects, memory 220 may be configured to store instructions that cause processor 205 to perform process 300, or portions thereof, as described below. In the illustrated embodiment, memory 220 includes a filtering module 221 that provides instructions to configure processor 205 to interpret and analyze data received from sensor module 210. Memory 220 can also include event parameter determination module 222 that provides instructions to configure processor 205 to determine external event parameters of an external event based on the sensor data interpreted and analyzed by the filtering module 221. Memory 220 further includes an event value determination module 224 that provides instructions to configure processor 205 to determine a representative event value based on the external event parameters. Memory 220 can also include a threshold determination module 225 that provides instructions to configure processor 205 to determine and/or specify a threshold value. In addition, memory 220 can include a dialing event determination module 226 that provides instructions to configure processor 205 to whether an external event is a dose dialing event based, at least in part, on the external event parameters and threshold value. It should be realized, that memory 220 is not limited to the above-identified modules, memory 220 may include additional, fewer, or combinations of modules that provide substantially similar instructions to configure processor 205 to perform substantially similar functions. The above discussed functions will be described in further detail below in reference to the above-identified modules depicted in FIG. 2.

The filtering module 221 includes instructions that configure the processor 205 to interpret and apply a filter to the data received from sensor module 210. Instructions in the filtering module 221 may configure the processor 205 to apply a low power filter to interpret the sensor waveforms representing an external event signature. Instructions in the filtering module 221 may also configure the processor to separate or split the external event signature into separate components, e.g., a direction component and a magnitude component. Therefore, instructions in the filtering module may be one means for interpreting, filtering, and analyzing the raw signal from sensor module 210.

Instructions in the event parameter determination module 222 configure the processor 205 to determine the external event parameters of the external event detected by sensor module 210. Instructions in the event parameter determination module 222 configure processor 205 to determine event parameters, based, at least in part, on the components determined in the filtering module 221. Event parameters may include the direction and the magnitude of the external event as detected by the sensor module 210. Therefore, instructions in the event parameter determination module 222 may represent one means for determining event parameters, based, at least in part, on the impulse experienced by injection device 100 as a result of an external event. The event parameter determination module 222 also may include instructions to configure the processor 205 to record event parameters in storage 280 or working memory 250.

Instructions in event value determination module 224 configure the processor 205 to determine a representative event value or score waveform, based, at least in part, on the event parameters. For example, the direction component waveform may be combined with the magnitude component waveform to form a score waveform attributed to the external event. Specifically, the event value determination module 224 may include instructions to configure the processor 205 to multiply a low frequency component with a high frequency component resulting in a score waveform.

Instructions in the threshold determination module 224 configure the processor 205 to specify a threshold value based, at least in part, on a predefined threshold. In one embodiment, the threshold value can be determined experimentally by performing a representative number of controlled studies to isolate the dose dialing events form any extraneous disturbances or events. The controlled studies can include measuring and/or monitoring controlled dose dialing events ("clicks"). In one embodiment, the threshold value can be determined as the lowest value of any of the controlled dose dialing events. In another embodiment, the threshold value may be determined as an average value of the controlled dose dialing events. In one embodiment, the threshold value may be previously determined and stored in storage 280 and/or working memory 250. The threshold determination module 224 may include instructions to configure processor 205 to retrieve the threshold value from storage 280 and/or working memory 250. In another embodiment, threshold determination module 225 may include instructions to configure the processor 205 to determine the threshold value, based on, at least in part, the controlled studies representing expected dose dialing events detected by sensor module 210. In yet another embodiment, threshold determination module 224 may include instructions to configure processor 205 to dynamically adjust the threshold value based on previously determined dose dialing events, e.g., by using event parameters determined by the processor 205 to be dose dialing events to dynamically update the threshold value. Therefore, the threshold determination module 224 represents one means for specifying a threshold value, based, at least in part, on expected daily handling of the injection device 100.

Instructions in the dialing event determination module 226 configure the processor 205 to determine whether an external event is a dialing dose based, at least in part, on the external event value and threshold value. The threshold value can be specified as a formula that represents the characteristics that an actual dose dialing event parameters must exceed for the processor 205 to recognize the external event as a dose dialing event. In one embodiment, instructions in the dialing event determination module 226 may configure the processor 205 to compare the external event value with the threshold value. If the external event value exceeds the threshold, the dialing event determination module 226 may provide instructions to configure the processor 205 to record the external event as a dialing event in working memory 250 or storage 280. Alternatively, if the comparison shows the external event value does not exceed the threshold value and, therefore, is not associated with a dose dialing event, then the processor 205 rejects the external event, e.g., when an accidental knock was detected by the sensor module 210. In another embodiment, dialing event determination module 226 may also include instructions to configure processor 226 to count or track the number of and direction of each external event. In one embodiment, the number of external events may be related to the selected dosage amount. In another embodiment, the number of external events may be factor in determining whether an external event is a dose dialing event or an extraneous external event. For example, a single isolated external event may represent an accidental knock, because it is unlikely that a single event relates to a dose dialing event. In this instance, a user is likely to increase or decrease the dosage amount by more than one dose dialing operation. Therefore, the dialing event determination module 226 represents a means for determining the occurrence of a dose dialing event and tracking the number of dose dialing events.

In an illustrative embodiment according to the present invention, processor 205 can also be configured to transmit data to communication module 260. The communication module 260 can be connected to a network by wired or wireless communication, cell communication, Bluetooth®, ZigBee®, LAN, WLAN, RF, IR, or any other communication method or system known in the art. In one embodiment, the communication module 260 is a BLE module which transfers data through Bluetooth® connectivity. In another embodiment, communication module 260 communicates data to a home health monitor with cloud connectivity.

In an illustrative embodiment according to the present invention, after receiving dose dialing event or injection event data the communication module 260 can transmit data to an external device 270. The external device 270 can be a mobile device, a home health monitor, a computer, a server, or any other external device. This allows device data to be transmitted to users, payers, pharmacists, physicians, nurses, family members or any other desired parties.

In an illustrative embodiment according to the present invention, external device 270 includes application 272, a display 274 and a communication module 278. External device 270 is configured to receive data from communication module 260 of module 110 via communication module 278 of the external device running application 272. In one embodiment, communication module 260 communicates with external device 270 through Bluetooth® connectivity. In one embodiment, display 274 allows the user to read data on the external device 270. In another embodiment, external device 270 can be a mobile telephone or tablet running application 272. In one embodiment, the device data is transmitted to an external device 270 of a user and, via application 272, the user determines if they would like to forward the information to payers, pharmacists, physicians, nurses, or other third parties. In another embodiment, application 272 allows a user to choose to whom the user would like to transmit data. In an alternative embodiment, the device data is transmitted directly to payers, pharmacists, physicians, nurses, or other third parties.

In an illustrative embodiment according to the present invention, data can be transmitted from module 110 to external device 270 through a series of steps. Communication module 260 receives data from the processor 205 or any component included in module 110. Communication module 260 then initiates a communication connection with communication module 278 of external device 270. Communication module 260 then transmits data to external device 270. External device 270 includes application 272 configured to accept the data from module 110, store the data in a computer readable memory of external device 270 or in the cloud, and display the data to the user through display 274. In another embodiment, external device 270 receives data from communication module 260 and after receiving the data, transmits the data to another location, such as a server computer.

Figure 3:
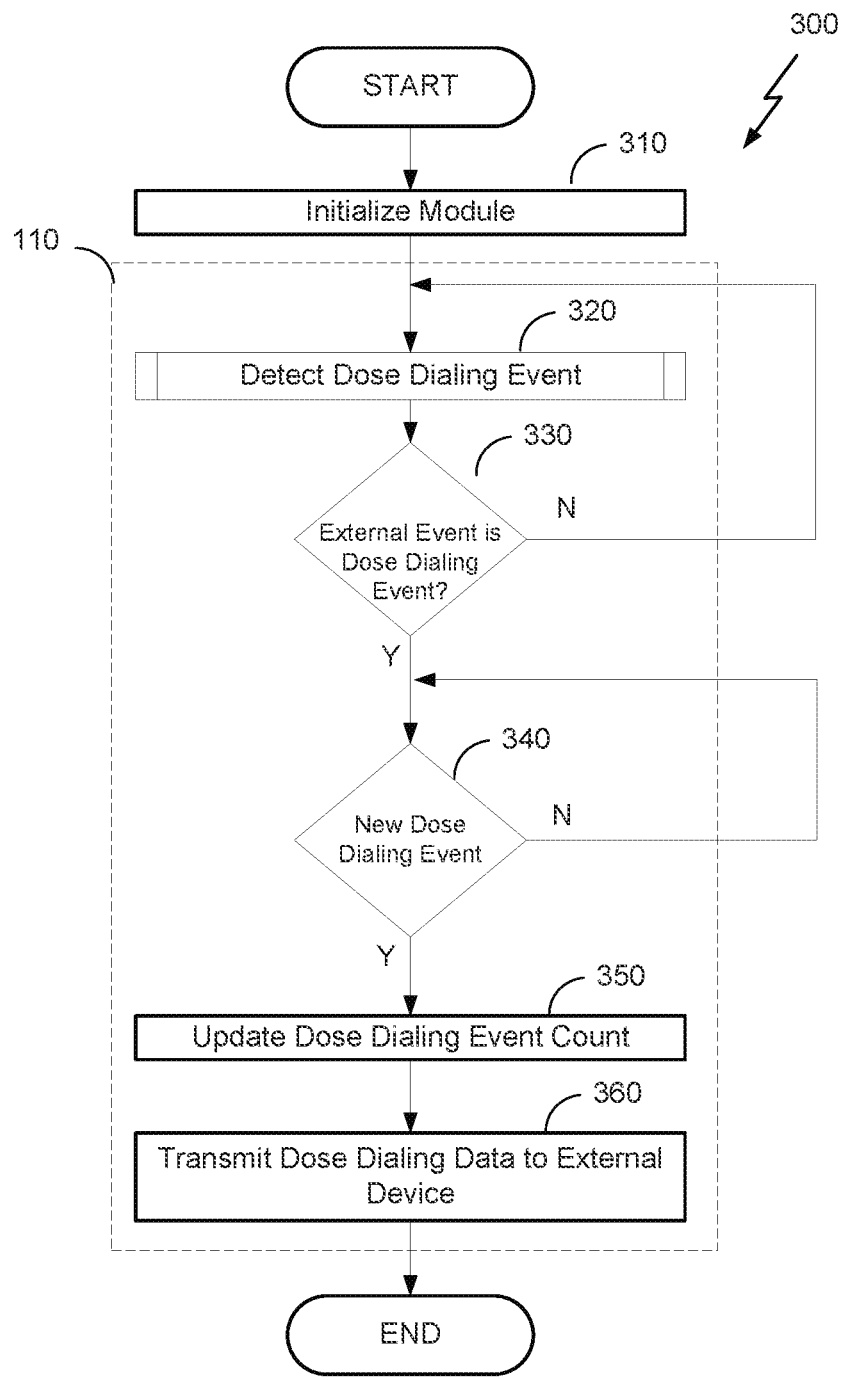
FIG. 3 depicts a flowchart of an embodiment of a system for monitoring the dosage amount selected on an injection device in accordance with an illustrative embodiment of the present invention.

FIG. 3 depicts a flowchart of a process 300 of an illustrative embodiment for a method of monitoring the dosage amount selected on an injection device such as the injection device 100 depicted in FIGS. 1-2. The process 300 begins at a start step, and then moves to step 310, wherein a module, such as the dose detection module 110, is initialized. In one embodiment, this initialization occurs when the module is placed on the exterior of an injection device, for example, by operating microswitch 106. In another embodiment, the module can be initiated mechanically by a user or other mechanical input. In an alternative embodiment, the module can be activated in response to a wireless communication received by a communication module of the module. In yet another embodiment, the module can be initiated upon the occurrence of an external event.

After initiation, the process moves to process step 320, wherein the module 110 is configured to detect a dose dialing event. Module 110 is configured to detect an external event and determine if the external event is a dose dialing event. The functions of step 320 will be explained in further detail below with reference to FIG. 4. After module 110 determines a dose dialing event has occurred at step 320, the process 300 moves to decision step 330, wherein a determination is made whether the external event was a dose dialing event. If the external event was not determined to be a dose dialing event, then the process returns to step 320 to continue monitoring for external events.

If a determination is made at decision step 330, that the external event was a dose dialing event, then the process 300 moves to decision step 340 wherein another determination is made whether the dose dialing event is a new dose dialing event. If the dose dialing event is not a new dose dialing event, then the system goes idle and remains at decision block 340 to continue to monitor for a new dose dialing event.

At decision step 340, the process 300 determines if the dose dialing event is a new dose dialing event. In one embodiment, a determination that a new dose dialing event has occurred is based on event parameters and a specified threshold value, both of which are determined as explained in further detail below in reference to FIGS. 4-6. Decision step 340 determines whether the event parameters at a given time have reduced below the specified threshold value. In one embodiment, the determination at decision step 340 is made by the dialing event determination module 226, whereby the dialing event determination module 226 continuously compares event parameters with the specified threshold. If the event parameters have not reduced below the specified threshold, then the process remains idle to continue to monitor the event parameters and threshold. If the determination at decision step 340 is that the event parameters have reduced below the specified threshold, then the process 300 determines the dose dialing event is a new event.

If a determination is made at decision step 340, that the dose dialing event is a new dose dialing event, then the process moves to step 350. At step 350, the dose dialing event is stored in the memory of the module, such as working memory 250 or storage 280. By storing the new dose dialing event the process 300 is able determine, track, and count a total dosage amount as a function of the event parameters. In this way, module 110 is able to record the number of times the user has operated the dose dialing mechanism (a dose dialing event) and the direction ("dialed up" or "dialed down") of such an operation.

After process 300 updates the dose dialing event count in step 350, process 300 moves to step 360, wherein dose dialing data is transmitted to an external device. The transmission can be managed by a communication module, such as communication module 260 depicted in FIG. 2. The external device can be a mobile phone, computer, or server, such as external device 270 depicted in FIG. 2. While not shown in the embodiment of FIG. 3, it should be realized that the user, payers, pharmacists, physicians, nurses, or other third parties may access the data through the external device to monitor and manage medicament regimen based on transmitted dose dialing data.

Figure 4:
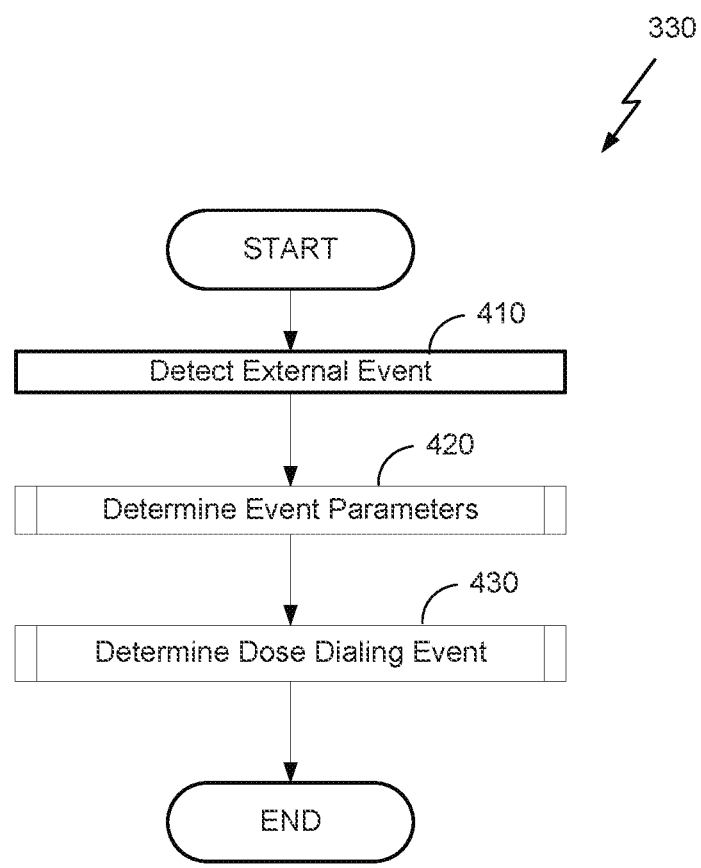
FIG. 4 depicts a flowchart of an embodiment of detecting a dose dialing event on an injection device in accordance with an illustrative embodiment of the present invention.

FIG. 4 depicts a flowchart of the process 330 of an illustrative embodiment according to the present invention of detecting a dose dialing event in an injection device. The process 330 begins at a start step, and then moves to step 410, wherein an external event is detected. The external event is detected by sensors included in module 110. For example, an external event can be detected by the sensor module 210 as depicted in FIG. 2. In one embodiment, a motion sensor and vibration sensor are configured to detect an impulse of mechanical energy propagating through an injection device as a result of an external event. The sensor module comprises one or more sensors including, but are not limited to, an accelerometer, microphone, temperature sensor, location proximity sensor, optical sensor, or the like. In one embodiment, sensor data is collected at a 30 kHz sampling frequency from a single axis accelerometer. In another embodiment, the processor 205 can be configured to receive the sensor data from sensor module 210 based on the detected external event, and record the sensor data in the working memory 250 or storage 280 for later access and on-board processing.

After the external event is detected by the sensors in step 410, the process 330 moves to step 420, wherein the event parameters are determined. The functions of process step 420 will be explained in further detail below with reference to FIG. 5. After the module 110 analyzes the external event in process step 420, the process moves to process step 430, wherein the module 110 determines if the external event is a dose dialing event or an extraneous event. The functions of process step 430 will be explained in further detail below with reference to FIG. 6.

Figure 5:
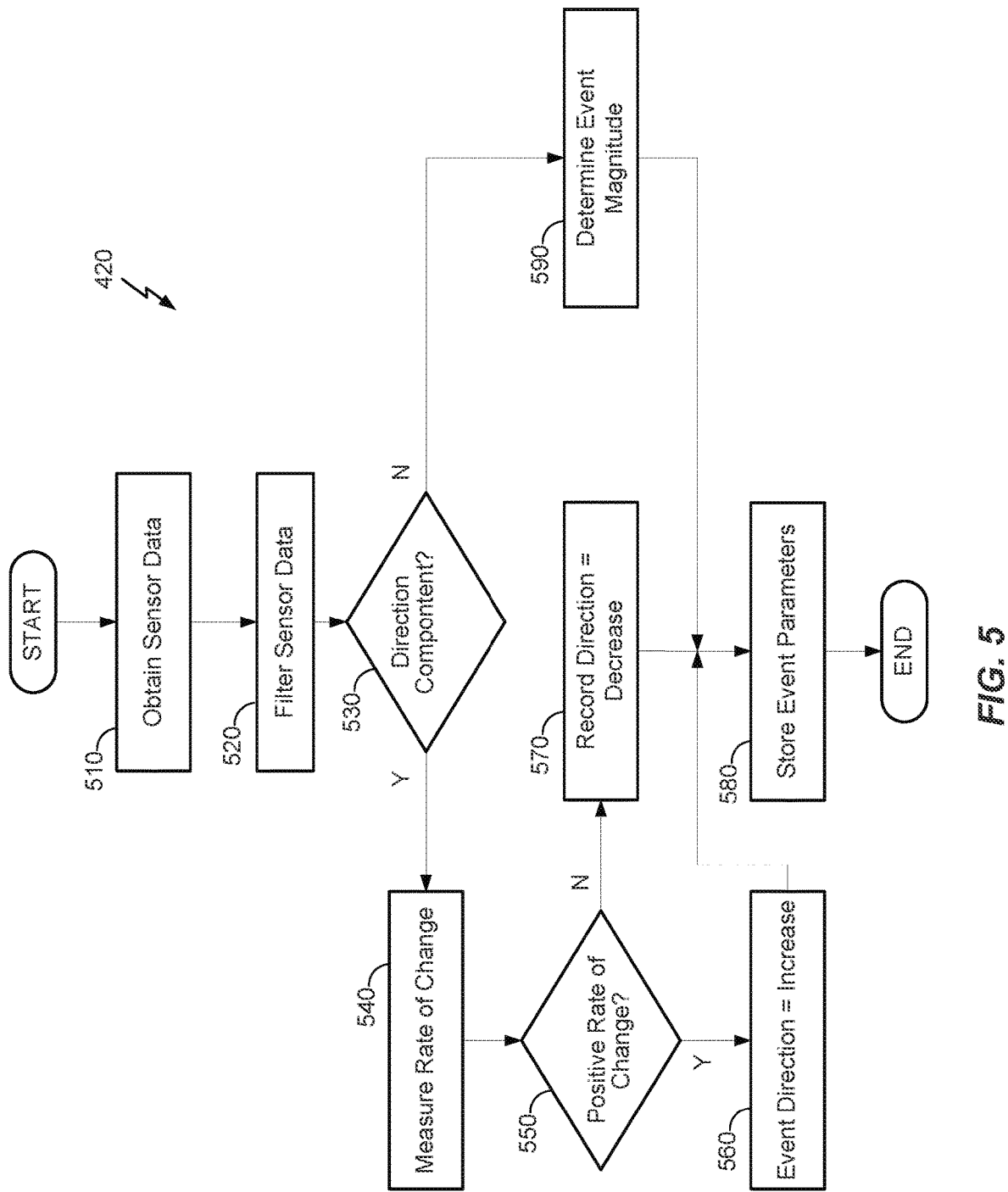
FIG. 5 depicts a flowchart of an embodiment of determining event parameters in an injection device in accordance with an illustrative embodiment of the present invention.

FIG. 5 depicts a flowchart of the process 420 of an illustrative embodiment of determining event parameters of an external event. In one embodiment, the external event is analyzed by the processor 205 configured based on instructions from the filtering module 221 and event parameters module 222. The process 420 beings at a start step, and then moves to step 510, wherein the sensor data is obtained from the sensors of a module, such as the sensor module 210 depicted in FIG. 2. In one embodiment, the processor 205 can retrieve the sensor data from working memory 250.

After the sensor data has been obtained, the process 420 moves to step 520, wherein the sensor data is filtered. In one embodiment the sensor data comprises a signature of the external event that is transmitted to a small, low power filtering unit, such as filtering module 221 depicted in FIG. 2.

In an illustrative embodiment according to the present invention, the sensor data is filtered and split into two components. One component, termed the "direction component" represents the data related to the direction of the external event. In one embodiment, the direction component is a low frequency waveform of the sensor data. Low frequency sensor data may include information about the overall motion of the accelerometer. In an illustrative embodiment according the present invention, the overall motion of one or more accelerometers may represent a "click direction" or direction of movement on the dose dialing mechanism. In another embodiment, the low frequency component may be sensor data having a frequency of less than 100 Hz.

A second component, the "magnitude component", can represent the data related to the magnitude of the external event. In one embodiment, the magnitude component is a high frequency waveform of the sensor data. High frequency sensor data may include information about the vibrations in the audible frequency range. In an illustrative embodiment according the present invention, the vibrations in the audible range may represent a "click sound" or the sound resulting from movement on the dose dialing mechanism. The vibrations may be vibrations in the air surrounding module 110 or vibrations that propagate through the injection device body. In another embodiment, the high frequency component may be sensor data having a frequency greater than 4 kHz.

After the sensor data is filtered, the process 420 moves to decision step 530, wherein a determination is made whether the component is a direction component. The determination can be performed by a processor, such as processor 205 depicted in FIG. 2. If the determination is made that the direction component is to be processed, the process 420 moves to step 540, wherein the direction component of the external event is processed. At decision step 530, if the determination is not made that the direction component is to be processed, then the process 420 moves to step 590, wherein the magnitude component of the external event is determined. While FIG. 5 depicts decision step 530 as a determination whether the direction component is to be processed, it should be realized decision step 530 may be configured as a determination whether the magnitude component is to be processed. In this embodiment, a positive determination would cause process 420 to move to step 590, while a determination in the negative moves process 420 to step 540.

Steps 540 to 570 determine the direction parameter of the external event. In an illustrative embodiment according to the present invention, process 420, at step 540, measures the rate of change of the direction component. In one embodiment, the process 420 measures the rate of change of a low frequency component of the signal detected by the sensor module. In one embodiment not shown in FIG. 5, the rate of change measured in step 540 can be compared with a specified rate of change. The specified rate of change can function as a threshold value used to pass/fail a direction component as being associated with a dose dial event. The specified rate of change can be determined through experimentation, e.g., measuring the rate of change of known dose dialing events to establish a threshold rate of change as the lowest measured rate of change. In a dose dialing event, the sensor module (e.g., sensor module 210) detects a signal representing an external event, and if that signal's rate of change, increase or decrease, is faster than the threshold rate of change then the external event represents a dose dialing event. Alternately, if the sensor module collects a signal that's rate of change is slower than the specified rate of change, then the external event is rejected as not pertaining to a dose dialing event. In an illustrative embodiment according to the present invention, the specified rate of change may be stored in the working memory 250 or storage 280 and accessed by processor 205. In another embodiment, the specified rate of change may be based on the slew rate of module 110.

After the rate of change is measured, the process 420 moves to decision step 550, wherein a determination is made whether the direction component's rate of change is a positive rate of change.

If the determination is made that the direction component's rate of change is a rate of change having positive values, then process 420 moves to step 560, wherein the direction component is determined to be an increase. In one embodiment, the determination that the direction is an increase represents that the sensor module detected movement from the external event that mimics or appears to be movement associated with operating the dose dialing mechanism to increase the dose of an injection device by one unit. In one embodiment, an increase designation may be a "dial up" or "clockwise" operation of the dose dialing mechanism.

If the determination is made that the direction component's rate of change is not a rate of change having positive values, e.g., the rate of change is negative, then process 420 moves to step 570, wherein the direction component is determined to be a decrease. In one embodiment, the determination that the direction is a decrease represents that the sensor module detected movement from an external event that mimics or appears to be movement associated with operating the dose dialing mechanism to decrease the dose of an injection device by one unit. In one embodiment, an increase designation may be a "dial down" or "counterclockwise" operation of the dose dialing mechanism. While FIG. 5 depicts decision step 550 as a determination whether the rate of change is positive, it should be realized decision step 550 may be configured as a determination whether the rate of change is negative. In this embodiment, a positive determination would cause process 420 to move to step 570, while a determination in the negative moves process 420 to step 560.

If the determination at decision step 530 results in processing the magnitude component, then process 420 moves to block 590, wherein the event magnitude is determined. In an illustrative embodiment according the present invention, the magnitude component may be related to the high frequency component of the sensor data, as detailed above. The high frequency component can be transformed (via envelope detection and integration as known in the art) to generate a waveform. The magnitude (or loudness) of the external event may be derived from the resulting waveform. It should be realized, the above description is merely one embodiment, and other method may be used to measure the magnitude component of the external event.

Figure 6:
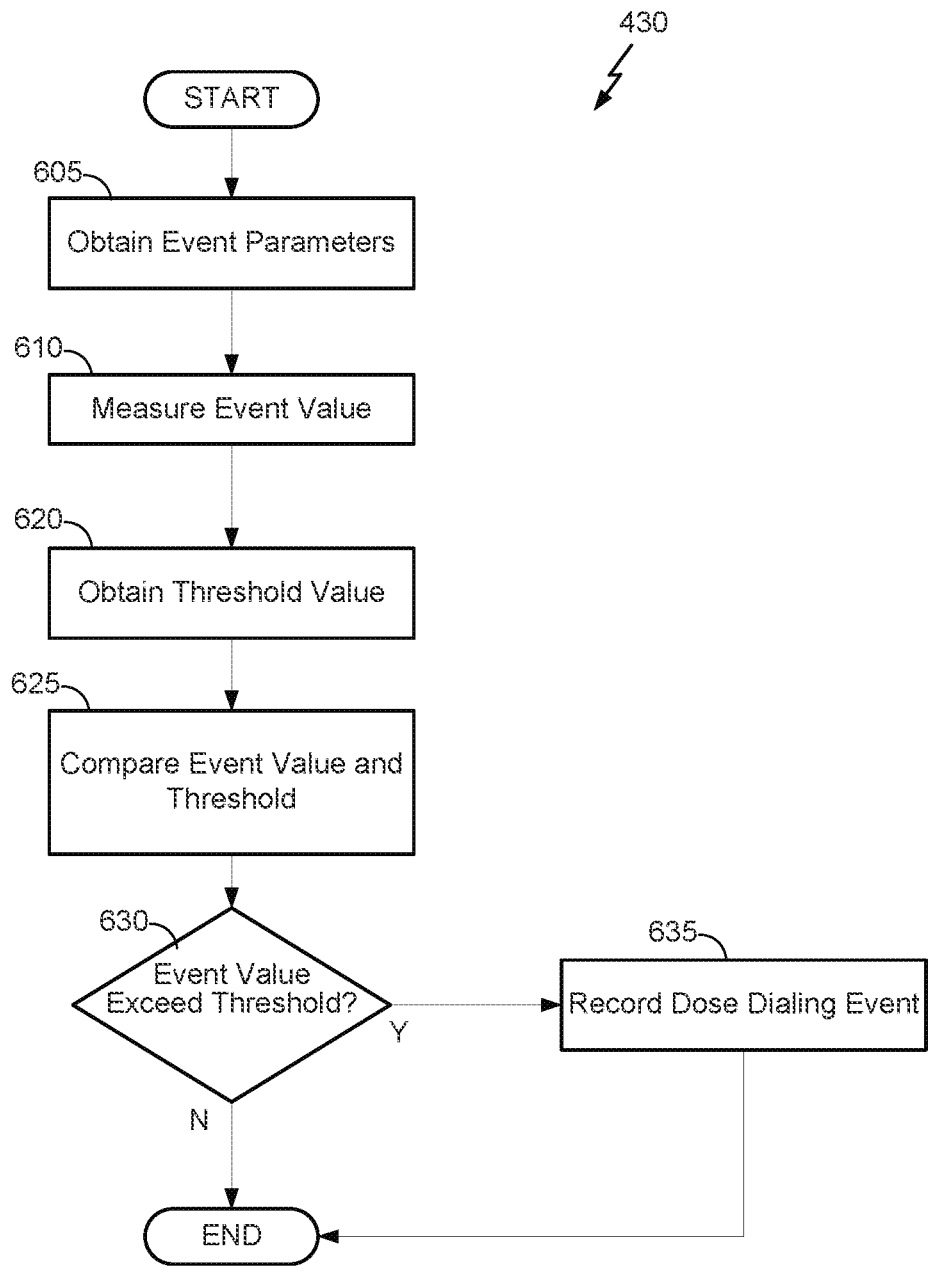
FIG. 6 depicts a flowchart of an embodiment of determining an event is a dose dialing event in accordance with an illustrative embodiment of the present invention.

After the external event direction and magnitude parameters are determined, the process 420 moves to step 580, wherein the event parameters are stored in a memory of the module, such as memory 250 depicted in FIG. 2. After the event parameters, including but not limited to, the magnitude and direction of the external event are stored, the process 420 concludes at the ends step FIG. 6 depicts a flowchart of the process 430 of an illustrative embodiment of determining an event is a dose dialing event. In one embodiment, a dose dialing event is determined by the processor 205 having retrieved data from working memory 250 or storage 280 and configured based on instructions from the event determination module 225, threshold determination module 225, and dialing event determination module 226.

The process 430 beings at a start step, and then moves to step 605, wherein the event parameters are obtained from a memory, such as working memory 205 depicted in FIG. 2. In one embodiment, processor 205 is configured to access working memory 250 to obtain event parameters determined in accordance with FIG. 5.

After the event parameters are obtained, the process moves to step 610, wherein an event value is measured based on the event parameters. In one embodiment, processor 205 can be configured to retrieve event parameters, including the direction component and magnitude component, and combine the event parameter components to determine an event value or score. In an illustrative embodiment according to the present invention, the low frequency waveform component is multiplied with the high frequency waveform component. The resulting waveform represents a scoring waveform associated with the sensor data of the external event being processed. In another embodiment, the event value may be based on the rate of change detected by the sensor module (e.g., sensor module 210) associated with the motion and/or vibrations imparted on the injection device due to the external event.

After the event value or score is determined, the process 430 moves to step 620, wherein a threshold value is obtained. In an illustrative embodiment according to the present invention, instructions in the threshold determination module 224 can configure the processor 205 to obtain a threshold value based, at least in part, on a specified threshold. In one embodiment, the threshold value may be predetermined and stored in storage 280 and/or working memory 250. The threshold value can be experimentally predetermined by running a representative number of controlled studies to isolate the dose dialing events form any extraneous disturbances or event. The controlled studies can include measuring and/or monitoring controlled dose dialing events ("clicks"). In one embodiment, the threshold value can be determined as the lowest value of any of the controlled dose dialing events. In another embodiment, the threshold value may be determined as an average value of the controlled dose dialing events. In another embodiment, threshold determination module 225 may include instructions to configure the processor to determine the threshold value, based on, at least in part, controlled studies representing expected dose dialing events. In yet another embodiment, the threshold value may be based on an expected rate of change associated with known dose dialing event.

After the threshold value is obtained, process 430 moves to step 635, wherein the event value and threshold value are compared. In one embodiment, the processor 205 can be configured to access the event and threshold values stored in working memory 250 or storage 280. In another embodiment, the threshold value may be specified as a formula used to compare the event value with the threshold formula. The event value may be represented by a scoring waveform as detailed above. In yet another embodiment, the threshold value may be a predetermined rate of change associated with expected dose dialing events.

Based on the comparison in step 625, process 430 moves to decision step 630, wherein a determination is made whether the event value exceeds the threshold. The determination can be performed by a processor, such as processor 205 depicted in FIG. 2. If a determination is made that the event value does not exceed the threshold, the process 430 rejects the external event and concludes at an end step. The process then moves to decision step 330 as depicted in FIG. 3.

If the determination is made that the event value exceeds the threshold, then process 430 moves to step 635, wherein the external event is recorded as a dose dialing event. In one embodiment, a processor can record the external event as a dose dialing event in a memory, such as processor 205 and working memory 250 depicted in FIG. 2. In this way, the module is able to recognize an external event as a dose dialing event based on event parameters and determine the direction of the dose dialing event. Thus, the module is capable of counting each operation of a dose dialing mechanism and the direction of such operation, thereby counting a total selected dose amount of an injection event. In an illustrative embodiment according the present invention, a dose dialing event can be recorded when the event value exceeds the threshold value and is the largest event value within a 2 ms time frame. In this way, the module continuously monitors the event value of an external event and compares the value to preceding and subsequent event values to determine whether an event value is the largest value within a specified time window. After the dose dialing event is recorded, the process 430 concludes at an end step and the process moves to decision step 330 as depicted in FIG. 3.

In another illustrative embodiment according to the present invention, additional sensor data may be processed in process 300 to provide additional event parameters in evaluating an external event. For example, sounds that are unique to the injection device functions, e.g., removal of the safety cap or injecting medicament, may be detected and processed. Such sounds may indicate that the detected external event relates to an extraneous event (e.g., an injection event) opposed to a do dialing event. In another embodiment, motion or vibrations associated with removing the safety cap may be detected and processed. Such movement may indicate that the external event is associated with an injection event and not a dose dialing event. In yet another embodiment, device orientation and motion may be detected and processed. For example, the orientation of an injection device being used for an injection event would provide data that is distinct from data associated with a dose dialing event. In accordance with the above examples, process 300 may be configured with additional detection means to isolate a dose dialing event from other extraneous events. It should be realized that although illustrative examples are provided, the process 300 can be configured with detection means to support the isolation of a dose dialing event from other events.

FIGS. 7A-D depict graphs illustrating dose dialing event signatures in accordance with an embodiment of the present invention. Each of the FIGS. 7A-7D illustrate vibration frequencies as detected by a sensor plotted against time.

FIG. 7A illustrates an increase in dose resulting from a user performing two clicks out, in other words by a user operating a dose dialing mechanism to increase the dose by two units. While there is manageable noise, as seen in the graph, there are two distinct events 710*a* and 710*b* that represent separate dose dialing events. In one embodiment, module 110 detects the dose dialing event by utilizing sensors to detect the event and interpret the signature by filtering and applying an algorithm as detailed herein. FIG. 7B is similar to FIG. 7A, but depicts four dose dialing events caused by the user dialing the dose up by four increments. FIGS. 7C and 7D represent instances of a user decreasing the selected dose by dialing down the dose dialing mechanism or performing "clicks in."

Figure 8:
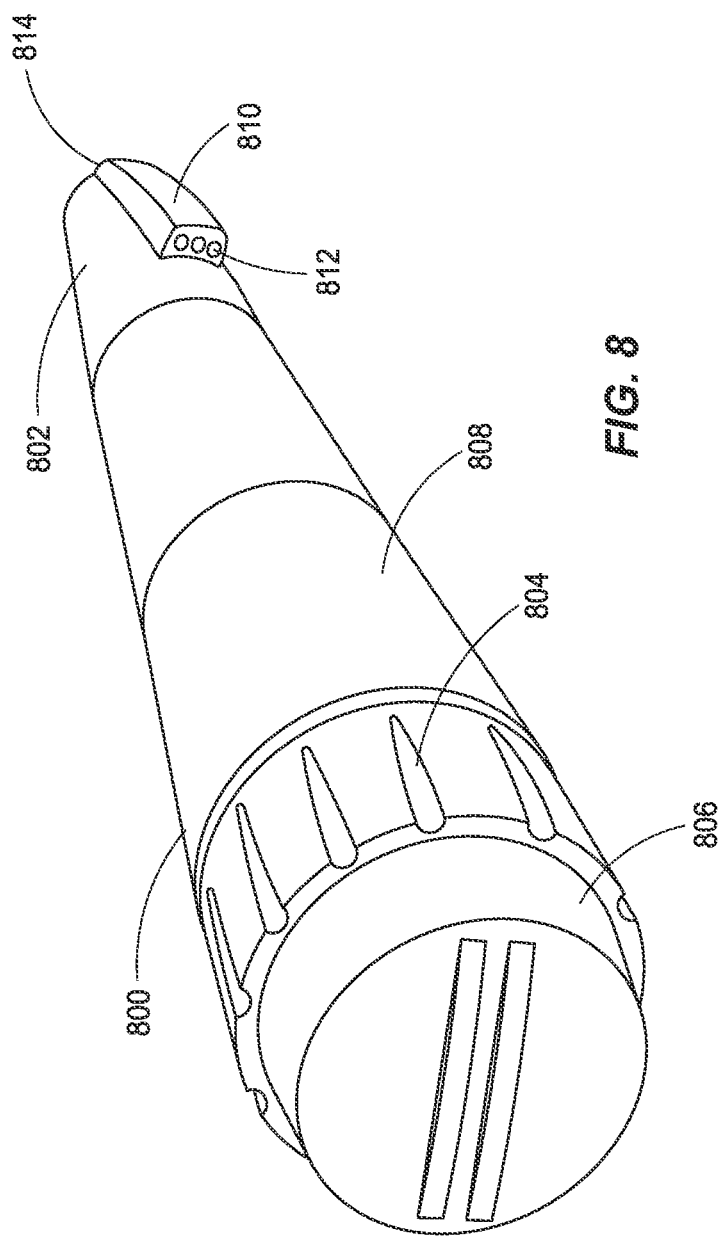
FIG. 8 depicts an alternate embodiment of an injection device with a module built into the cap in accordance with an illustrative embodiment of the present invention.

FIG. 8 depicts an illustrative embodiment of an injection device 800 according to the present invention. The injection device 800 comprises the same features as injection device 100. Injection device 800 comprises a body 808 having an injecting button 806 positioned on one end of the injection device 800. Injecting button 806 is substantially similar to injecting button 106. Injection device 800 also includes dose dialing mechanism 804 configured to allow a user to dial an injection dose. Dose dialing mechanism 804 operates substantially similar to dose dialing mechanism 104. At the distal end of body 808 is a smart cap 802 configured to prevent the user form inadvertent contact with the syringe.

In an illustrative embodiment according to the present invention, injection device 800 comprises module 810. Module 810 comprises the substantially the same features and is configured to operate in substantially the same manner as module 110. However, module 810 is designed into or as part of smart cap 802. In this embodiment, module 810 is attached to the injection device body 808 without changing the exterior size or form of the injection device 800 or preventing the function of injection device 800. In an illustrative embodiment according to the present invention, the injection device 800 can be the PHYSIOJECT™ autoinjector, VYSTRA™ Disposable Pen, or Reusable Pen from Becton Dickinson. Although it should be realized that other injector devices are also contemplated within the scope of the invention.

Module 810 allows a user to view one or more status indicators 812 located on the module 810. The one or more status indicators may be part of the module 810 and can indicate a conditions or state of the device. The status indicators 812 may include one or more lights, such as light-emitting diodes ("LEDs") or any other visual, auditory, or tactile stimuli. The condition or state of use may include, but is not limited to, out-of-range conditions (e.g., a loss of connectivity) or temperature alerts. Indicator 812 may operate in substantially the same manner as indicators 112.

In another illustrative embodiment according to the present invention, the module 810 may include a microswitch (not shown). The microswitch may be operated to activate dosage detection module 810. In one embodiment, microswitch may be operated upon placing the smart cap 802 onto injection device 800. In this regard, the module 810 may be activated when smart cap 802 is positioned on injection device 800, thereby protecting the syringe, and deactivated when the smart cap 802 is removed for an injection event. By deactivating module 810 upon removal of smart cap 802, subsequent external events are not detected by module 810 and movement of the injection device 800 to administer an injection event are removed from the dose dialing event determination algorithm. In another embodiment, the removal of smart cap 802 may not deactivate module 810, thereby permitting continuous uninterrupted monitoring of injection device 800. In this embodiment, removing smart cap 802 to administer an injection event may cause a state-of-device indicator to be transmitted to the module 810 to indicate that any external movements detected after removal of smart cap 802 are extraneous or injection events and not dose dialing events.

The above detailed description is directed to certain specific embodiments of the invention. However, the invention can be embodied in a multitude of different ways. It should be apparent that the aspects herein may be embodied in a wide variety of forms and that any specific structure, function, or both being disclosed herein is merely representative. Based on the teachings herein one skilled in the art should appreciate that an aspect disclosed herein may be implemented independently of any other aspects and that two or more of these aspects may be combined in various ways, without materially departing from the novel teachings and advantages of this invention. Accordingly, all such modifications are intended to be included within the scope of the invention. For example, an apparatus may be implemented or a method may be practiced using any number of the aspects set forth herein. In addition, such an apparatus may be implemented or such a method may be practiced using other structure, functionality, or structure and functionality in addition to or other than one or more of the aspects set forth herein.

Further, the systems and methods described herein may be implemented on a variety of medicament delivery or injection devices. These include insulin injection devices for diabetes, as well as injection devices designed for other diseases.

Furthermore, the system and methods described herein may be implemented by a medicament delivery or injection device in communication with a computing device. These include mobile and non-mobile devices, as well as general purpose or special purpose computing system environments or configurations. Examples of computing systems, environments, and/or configurations that may be suitable for use with the invention include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like. Further, the systems and methods may be implemented in mobile devices (e.g., phones, smartphones, Personal Digital Assistants (PDAs), Ultra-Mobile Personal Computers (UMPCs), Mobile Internet Devices (MIDs), etc.).

It should be understood that any reference to an element herein using a designation such as "first," "second," and so forth does not generally limit the quantity or order of those elements. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements. In addition, terminology of the form "at least one of: A, B, or C" used in the description or the claims means "A or B or C or any combination of these elements."

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

As used herein, a phrase referring to "at least one of" a list of items refers to any combination of those items, including single members. As an example, "at least one of: a, b, or c" is intended to cover: a, b, c, a-b, a-c, b-c, and a-b-c.

The steps of a method or process described in connection with the implementations disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of non-transitory storage medium known in the art. An exemplary computer-readable storage medium is coupled to the processor such the processor can read information from, and write information to, the computer-readable storage medium. In the alternative, the storage medium may be integral to the processor. The processor and the storage medium may reside in an ASIC. The ASIC may reside in a user terminal, camera, or other device. In the alternative, the processor and the storage medium may reside as discrete components in a user terminal, camera, or other device.

If implemented in software, the functions may be stored on or transmitted over as one or more instructions or code on a computer-readable medium. The steps of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein. The word "exemplary" is used exclusively herein to mean "serving as an example, instance, or illustration." Any implementation described herein as "exemplary" is not necessarily to be construed as preferred or advantageous over other implementations. Additionally, a person having ordinary skill in the art will readily appreciate, the terms "upper" and "lower" are sometimes used for ease of describing the figures, and indicate relative positions corresponding to the orientation of the figure on a properly oriented page, and may not reflect the proper orientation of the IMOD as implemented.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Headings are included herein for reference and to aid in locating various sections. These headings are not intended to limit the scope of the concepts described with respect thereto. Such concepts may have applicability throughout the entire specification.

The previous description of the disclosed implementations is provided to enable any person skilled in the art to make or use the present invention. Various modifications to these implementations will be readily apparent to those skilled in the art, and the generic principles defined herein may be applied to other implementations without departing from the spirit or scope of the invention. Thus, the present invention is not intended to be limited to the implementations shown herein but is to be accorded the widest scope consistent with the principles and novel features disclosed herein.

What is claimed is:

1. A method for determining an occurrence of an event in a medical device comprising:
   detecting a direction of an impulse transmitted through the medical device; and determining an occurrence of the event in the medical device based at least in part on the detected direction of the impulse transmitted through the medical device.

2. The method of claim 1, further comprising detecting a magnitude of the impulse.

3. The method of claim 2, wherein determining the occurrence of the event is based at least in part on the magnitude of the impulse.

4. The method of claim 3, wherein determining the occurrence of the event comprises comparing data based on the magnitude and direction of the impulse to a threshold value, wherein occurrence of the event is detected only when the data exceeds the threshold value.

5. The method of claim 4, wherein the event comprises a dose dialing event.

6. The method of claim 4, further comprising determining an occurrence of an unintentional movement of the medical device when the data based on the magnitude and direction of the impulse is below the threshold value.

7. The method of claim 1, wherein the event comprises a dose dialing event.

8. The method of claim 7, further comprising distinguishing between a dose increasing event and a dose decreasing event based on the detected direction of the impulse.

9. The method of claim 7, wherein the event comprises a rotation of a dose dialing mechanism, the method further comprising determining a direction of rotation of the dose dialing mechanism based on the detected direction of the impulse.

10. A system for determining the occurrence of an event in a medical device, comprising:
one or more sensors configured to detect a direction of an impulse transmitted through a medical device and generate sensor data based on the direction of the impulse; and
a processor configured to:
obtain the sensor data from the one or more sensors;
determine an occurrence of the event in the medical device based at least in part on the detected direction of the impulse transmitted through the medical device.

11. The system of claim 10, wherein the one or more sensors are mounted on a carrier configured to fit on an exterior of the medical device.

12. The system of claim 10, wherein the one or more sensors are part of a cap of the medical device.

13. The system of claim 10, wherein the one or more sensors are part of a module configured to attach to the medical device, wherein the module is configured to be activated when the module is attached to the medical device.

14. The system of claim 10, wherein the one or more sensors are configured to detect a magnitude of the impulse.

15. The system of claim 14, wherein the processor is configured to determine the occurrence of the event based at least in part on the detected magnitude of the impulse.

16. The system of claim 15, wherein the processor is configured to determine the occurrence of the event by comparing data based on the magnitude and direction of the impulse to a threshold value, wherein occurrence of the event is detected only when the data exceeds the threshold value.

17. The system of claim 16, wherein the event comprises a dose dialing event.

18. The system of claim 16, wherein the processor is configured to determine an occurrence of an unintentional movement of the medical device when the data based on the magnitude and direction of the impulse is below the threshold value.

19. The system of claim 10, wherein the event comprises a dose dialing event.

20. The system of claim 19, wherein the processor is configured to distinguish between a dose increasing event and a dose decreasing event based on the detected direction of the impulse.

21. The system of claim 19, wherein the event comprises a rotation of a dose dialing mechanism, wherein the processor is configured to determine a direction of rotation of the dose dialing mechanism based on the detected direction of the impulse.

* * * * *